United States Patent
Truckai et al.

(10) Patent No.: US 11,832,786 B2
(45) Date of Patent: Dec. 5, 2023

(54) ENDOSCOPIC IMAGING AND CONTROL SYSTEMS AND METHODS FOR USE IN DIAGNOSTIC AND THERAPEUTIC MEDICAL PROCEDURES

(71) Applicant: Meditrina, Inc., San Jose, CA (US)

(72) Inventors: Daniel Truckai, Saratoga, CA (US); Akos Toth, Cupertino, CA (US); Csaba Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 313 days.

(21) Appl. No.: 17/150,970

(22) Filed: Jan. 15, 2021

(65) Prior Publication Data

US 2021/0219816 A1    Jul. 22, 2021

Related U.S. Application Data

(60) Provisional application No. 62/962,100, filed on Jan. 16, 2020.

(51) Int. Cl.
  *A61B 1/00* (2006.01)
  *A61B 5/06* (2006.01)
  *A61B 1/04* (2006.01)
  *A61B 1/06* (2006.01)

(52) U.S. Cl.
  CPC ...... *A61B 1/00006* (2013.01); *A61B 1/00009* (2013.01); *A61B 1/00042* (2022.02); *A61B 1/00045* (2013.01); *A61B 1/00068* (2013.01); *A61B 1/00105* (2013.01); *A61B 1/00128* (2013.01); *A61B 1/042* (2013.01); *A61B 1/0669* (2013.01); *A61B 5/067* (2013.01)

(58) Field of Classification Search
  CPC ............ A61B 1/00006; A61B 1/00009; A61B 1/00042; A61B 1/00045; A61B 1/00068; A61B 1/00105; A61B 1/00128; A61B 1/042; A61B 1/0669; A61B 5/067
  USPC .......................................................... 600/137
  See application file for complete search history.

(56) References Cited

U.S. PATENT DOCUMENTS

| | | | |
|---|---|---|---|
| 5,443,057 A * | 8/1995 | Elmore | A61B 1/00165 600/182 |
| 5,621,830 A * | 4/1997 | Lucey | A61B 1/317 600/137 |
| 6,030,339 A * | 2/2000 | Tatsuno | G02B 23/2484 600/112 |
| 7,387,605 B2 * | 6/2008 | Frith | A61B 1/00126 600/137 |
| 2002/0161280 A1 * | 10/2002 | Chatenever | A61B 1/042 600/137 |
| 2014/0066701 A1 * | 3/2014 | Wilson | A61B 1/000094 600/102 |
| 2015/0196197 A1 * | 7/2015 | Kienzle | A61B 17/3478 600/478 |
| 2018/0132700 A1 * | 5/2018 | Ouyang | A61B 1/0684 |
| 2019/0310681 A1 * | 10/2019 | Shainwald | A61B 17/3417 |
| 2020/0397232 A1 * | 12/2020 | Ulmschneider | A61B 90/03 |
| 2023/0128846 A1 | 4/2023 | Landgraf et al. | |

* cited by examiner

*Primary Examiner* — John P Leubecker
*Assistant Examiner* — Li-Ting Song
(74) *Attorney, Agent, or Firm* — Levine Bagade Han LLP

(57) ABSTRACT

Endoscopic viewing systems for use in diagnostic and therapeutic medical procedures. More specifically, an imaging and control system and coupler that allows for control of imaging and fluid management from a hand-held unit coupled to a conventional multiple-use, sterilizable endoscope.

12 Claims, 4 Drawing Sheets

ENDOSCOPIC IMAGING AND CONTROL SYSTEMS AND METHODS FOR USE IN DIAGNOSTIC AND THERAPEUTIC MEDICAL PROCEDURES

RELATED APPLICATIONS

This application is a non-provisional of U.S. Provisional No. 62/962,100 filed Jan. 16, 2020, the entirety of which is incorporated by reference.

FIELD OF THE INVENTION

The present invention generally relates to endoscopic viewing systems for use in diagnostic and therapeutic medical procedures. More specifically, the invention relates to an imaging and control system and coupler that allows for control of imaging and fluid management from a hand-held unit coupled to a conventional multiple-use, sterilizable endoscope.

SUMMARY OF THE INVENTION

The present disclosure includes endoscopic system. For example, such a system can include a handle with a rotatable C-mount coupler assembly for coupling to a proximal end of an endoscope; an image sensor carried by the rotatable C-mount coupler assembly; and at least one of an accelerometer and a gyroscope carried by the rotatable C-mount coupler assembly.

Variations of the system can include a controller and an image processor coupled to the image sensor and the at least one the accelerometer or the gyroscope; and a controller algorithm adapted to acquire signals from the at least one accelerometer or gyroscope caused by rotation of the C-mount coupler and thereafter rotate a displayed image in response to the signals to correct an orientation of the displayed image to a selected configuration.

The endoscopic system can further comprise electrical leads extending from the image sensor to a fixed location in the handle, wherein the electrical leads are configured with a slack portion in an interior of the handle to accommodate rotation of rotatable C-mount coupler assembly therein. The electrical leads can optionally extend from the at least one of the accelerometer or the gyroscope to a fixed location in the handle, wherein the electrical leads are configured with a slack portion in an interior of the handle to accommodate rotation of rotatable C-mount coupler assembly therein.

Variations of the system can include a rotatable C-mount coupler assembly that is configured to rotate at least 90° about its axis in the handle. In additional variations, the rotatable C-mount coupler assembly can rotate at least 180° about its axis in the handle.

Additional variations of the system include a fluid management system controlled by the controller, and at least one actuator in the handle for adjusting operating parameters of the fluid management system. The controller can also include algorithms for operating a fluid inflow source and a negative pressure source of the fluid management system to maintain fluid pressure in a working space within a set pressure range.

Additional variations of the system can further comprise a light source adapted for coupling to the endoscope and at least one actuator in the handle for adjusting operating parameters of light source.

The endoscopic system can further include at least one actuator in the handle for operating the image sensor to capture images or videos.

An additional variation of an endoscopic system can include a handle with a rotatable C-mount coupler assembly for coupling to a proximal end of an endoscope; an image sensor carried by the rotatable C-mount coupler assembly; at least one of an accelerometer and a gyroscope carried by the rotatable C-mount coupler assembly; and a controller and image processor coupled to the image sensor and the at least one of the accelerometer or the gyroscope, wherein a controller algorithm is adapted to acquire signals from the at least one of the accelerometer or the gyroscope caused by rotation of the C-mount coupler and thereafter rotate a displayed image in response to the signals to correct an orientation of the displayed image to a selected configuration.

The present disclosure also includes methods for orienting an endoscope image on a display. For example, such a method can include providing a C-mount coupler carrying an image sensor for displaying an image on a display, wherein the C-mount coupler carries at least one of an accelerometer and gyroscope carried by the C-mount coupler; attaching the C-mount coupler to an endo scope; acquiring signals from at least one of the accelerometer and the gyroscope caused by rotation of the C-mount coupler; and rotating the image on the display in response to the signals to correct an orientation to a selected configuration.

Variations of the method also include a C-mount coupler that is rotatably disposed in a handle member. Additional variations of the method include rotating the C-mount coupler and manipulating the image electronically.

BRIEF DESCRIPTION OF THE DRAWINGS

Additional aspects of the invention will become clear from the following description of illustrative embodiments and from the attached drawings, in which.

DETAILED DESCRIPTION OF THE INVENTION

Figure 1:
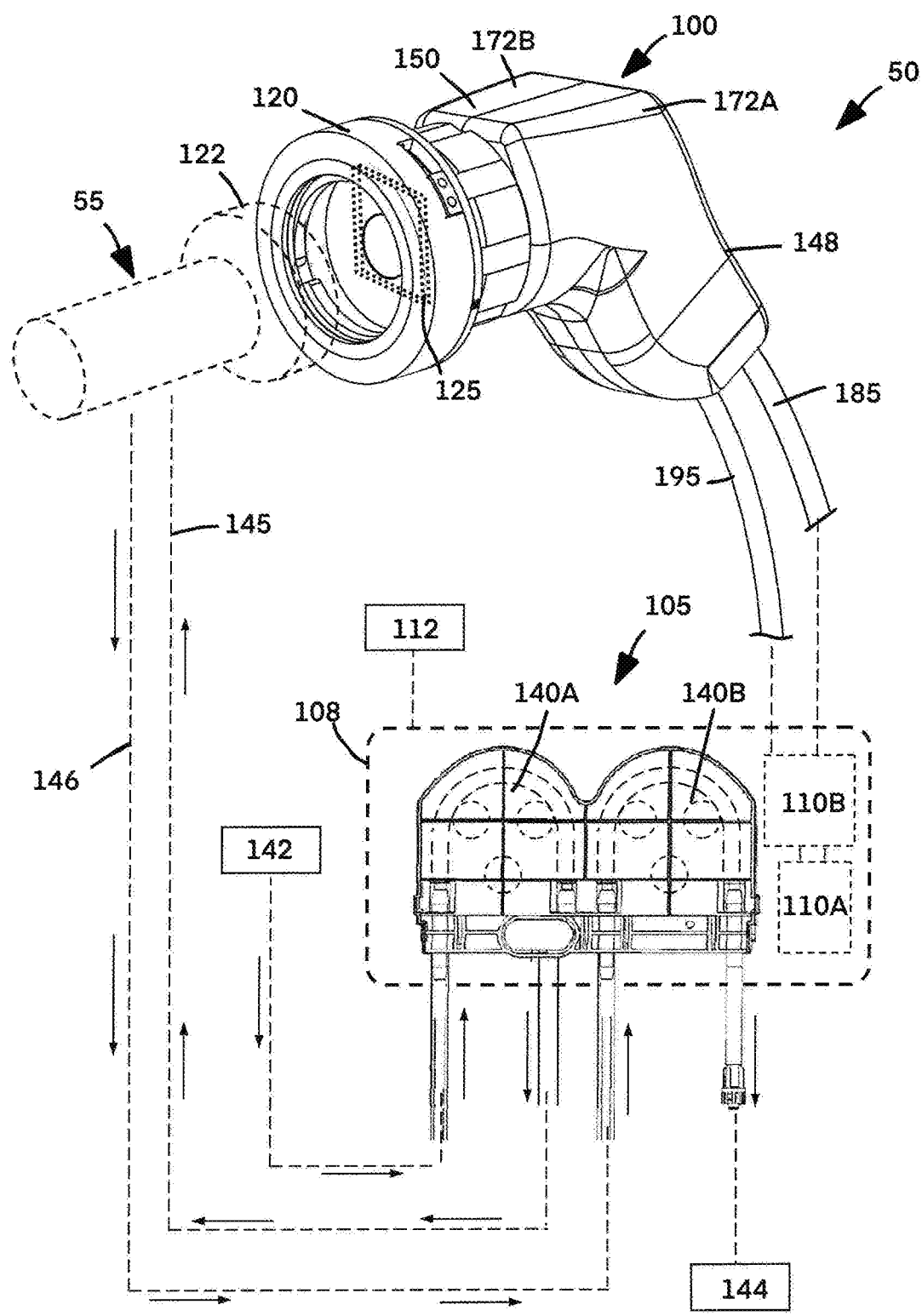
FIG. 1 illustrates components of an imaging system for hysteroscopic treatments corresponding to the invention, including a perspective view of a multi-functional handle component and a schematic view of a fluid management system.

FIG. 1 illustrates an imaging system 50 adapted for use with a conventional endoscope 55 to perform a hysteroscopic or endoscopic procedure corresponding to the invention, which comprises multiple components, including a handle component 100 and a fluid management system 105 housed in a base unit or console 108. The base unit 108 also carries a controller 110A and power source for operating the system 50 and can include an image processor 110B for processing signals from an image sensor carried by the system. A display 112 is coupled to the base unit 108 for viewing images provided by the system 50.

Figure 2:
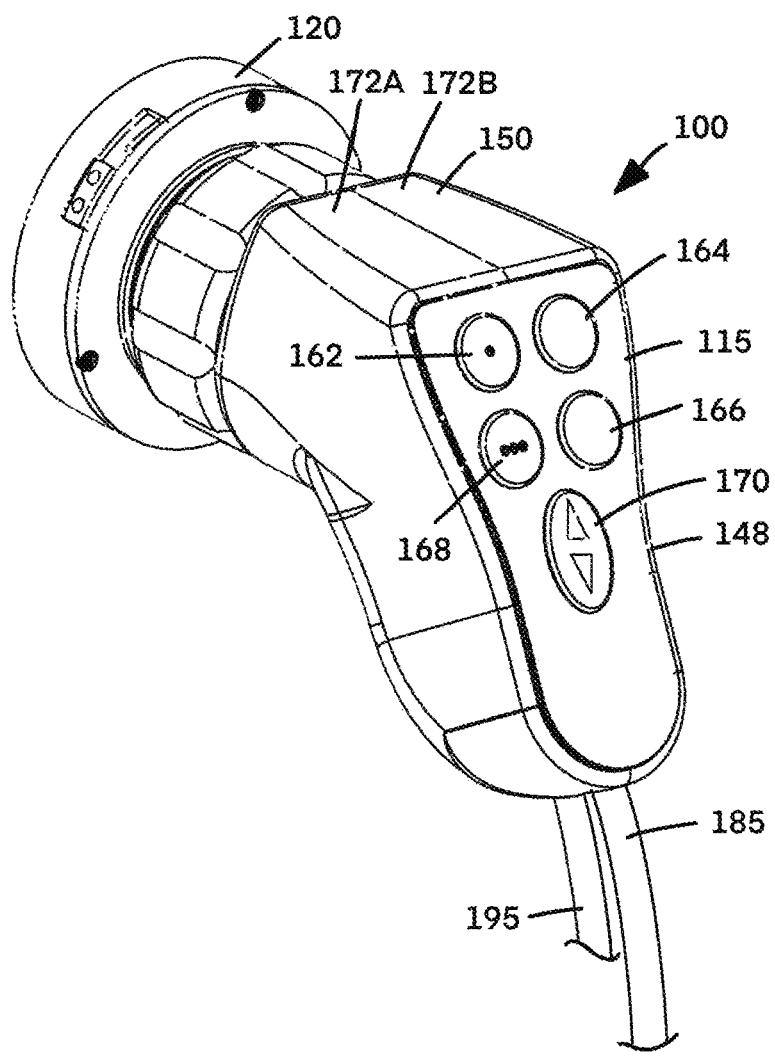
FIG. 2 is perspective view of the handle component from a different angle.

More in particular, the handle component 100 of FIGS. 1 and 2 can comprise a single-use or multiple-use handle unit 100 with a finger-actuated control pad 115 (FIG. 2) for operating the controller 110A and the fluid management system 105. The handle component 100 has a distal end comprising a C-mount coupler portion 120 adapted for coupling to a proximal end 122 of a commercially available, multi-use, sterilizable endoscope 55. The term "C-mount coupler" is used herein to describe a "camera mount" as is known in the art. In this variation, the handle component 100 carries an electronic image sensor 125 as will be described further below (see FIGS. 1 and 3). Various latch mechanisms are known for latching the C-coupler portion 120 to the endoscope 55.

Referring to FIG. 1, the fluid management system 105 includes a first peristaltic inflow pump 140A and second peristaltic outflow pump 140B, a fluid source 142 and fluid collection reservoir 144 which can include a fluid deficit measurement subsystem as is known in the art. Inflow tubing 145 extends to the endoscope 55 which has a flow channel therein to deliver fluid inflows to the patient's body, such as a uterine cavity in a hysteroscopy. Outflow tubing 146 is shown coupled to the endoscope 55 but also may be coupled to a tool introduced through the endoscope, depending on the procedure. In any event, the fluid management system in endoscope operate as is known in the prior art.

Referring to FIGS. 1-4, it can be seen that the handle component 100 has a grip portion 148 which extends from an upper housing portion 150. A rotating assembly 155 is carried within the upper housing 150 wherein image sensor 125 and lens 127 are disposed in the interior of the rotating assembly 155.

The grip portion 148 includes a finger or thumb-actuated control pad 115 that carries actuator buttons for operating multiple functions of the system 50, for example, including (i) operating the fluid management system 105, (ii) capturing images or videos from the image sensor 125, (iii) adjusting light intensity from a light source coupled to (or carried by) the endoscope 55 (not shown). As described above, the control unit 108 typically carries the image processor 110B. However, the interior of the handle 100 also can carry the image processor 110B or a processing component thereof.

Figure 3:
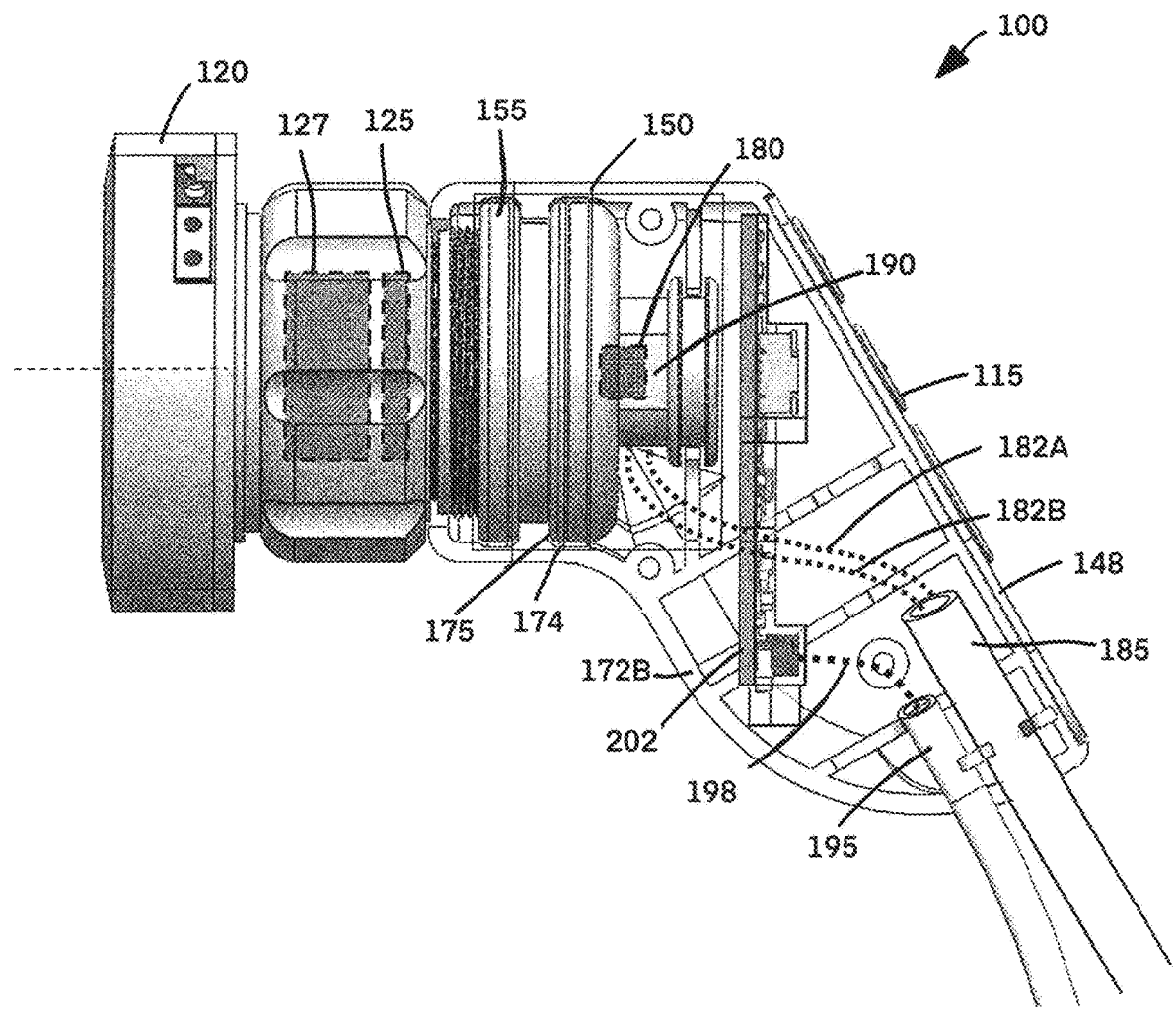
FIG. 3 is a side elevation view of the handle component of FIGS. 1-2 with a side of the handle shell removed to show a rotating assembly and a circuit board carried within the handle component.
Figure 4:
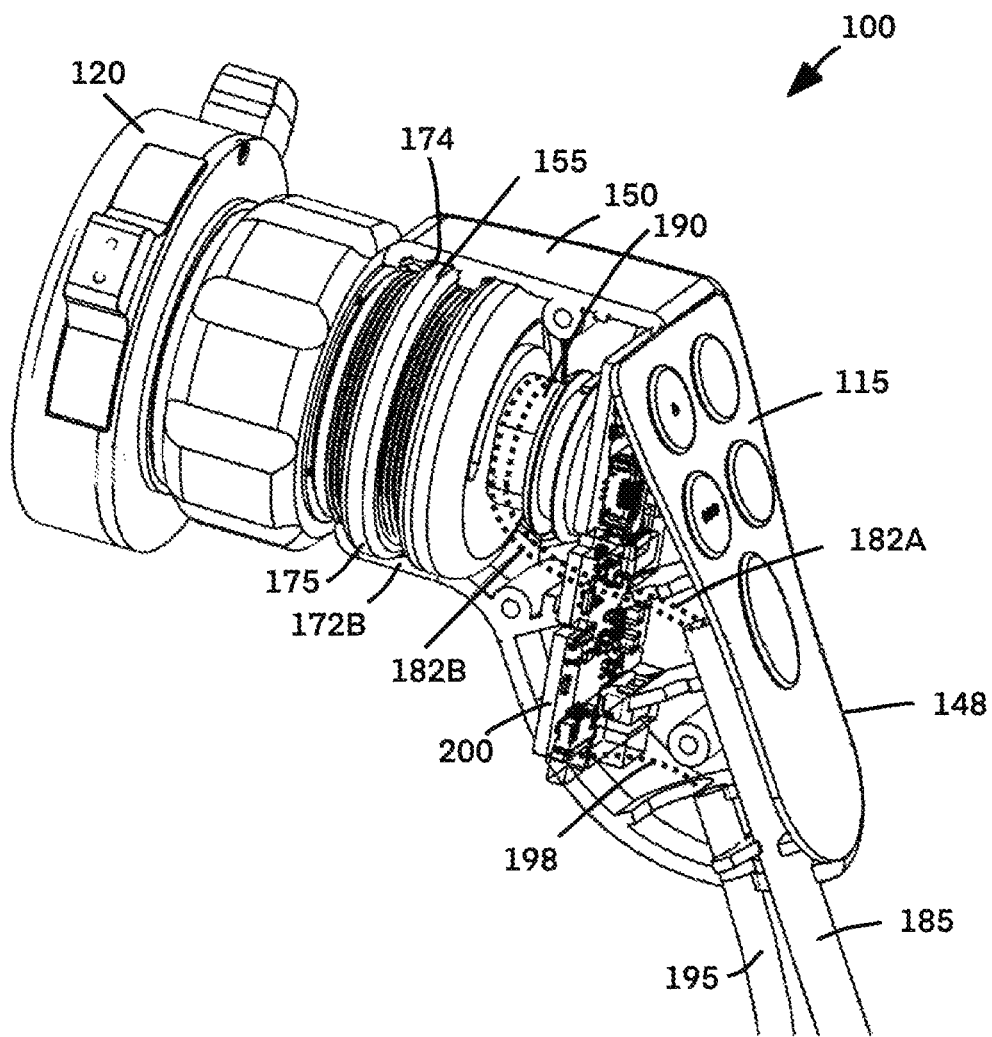
FIG. 4 is a perspective view of the endoscopic viewing system of FIG. 3 from a different angle illustrating the rotating shaft assembly and circuit board.

Referring to FIGS. 2-4, the view of the handle 100 show the control pad 115 with four actuator buttons or switches (162, 164, 166, 168) and one scrolling-actuator button 170 which are adapted to operate the system. In one variation, actuator 162 is adapted for turning on and off irrigation, or in other words actuating the fluid management system 105 to provide fluid inflow and fluid outflows. Actuator 164 is adapted for image or video capture. In a variation, momentary pressing the actuator 164 will capture a single image and longer pressure on the actuator will operate a video recording. Actuator 166 is adapted adjustment of light intensity. In one variation, actuator 168 is adapted for "flush", that is, providing a high flow rate through the inflow tubing as long as the button is depressed.

The scrolling-actuator button 170 has a scrolling function, wherein pressing the scrolling button 170 will cycle through various subsystems. In one example, the scrolling button 162 can be actuated to cycle through the following subsystems and features: (i) fluid inflow/outflow rate from the fluid management system 105; (ii) the set pressure which is to be maintained by fluid management system 105; (iii) fluid deficit alarm which is calculated by the fluid management system 105; and (iv) optional selection of still image capture or video capture. Then, after scrolling to select a subsystem, the physician can push centrally on the actuator to adjust by toggling through, or among, operating parameters of the selected subsystem. In one variation, the selection of subsystems, as well as the real-time operating parameters of each subsystem, will be displayed on a video monitor or display 112 as shown in FIG. 1. Thus, it can be understood that the physician may operate the scrolling button 170 to scroll through and select any subsystem or feature while observing such as selection on the display 112, and then actuate the scrolling-actuator 170 to adjust an operating parameter which also can be observed on the display 112.

In another aspect of the invention, the controller 110A includes a control algorithm for operating the control pad 115 which provides a jump back to a default condition after the scrolling-actuator button 170 has been used by the physician. For example, the default condition will be a selected default subsystem which is actuatable by the actuator 170. In one variation, the default subsystem is the fluid inflow/outflow rate, which may be the subsystem most commonly actuated by the physician to control fluid flow into and out of a working space. As described above, the physician may use the scrolling feature of button 170 to select any subsystem for adjustment of an operating parameter. If, however, the physician does not continue to scroll between the various subsystems or change a parameter within a predetermined time interval, then the control algorithm will jump back to the default subsystem, which may be the fluid inflow/outflow rate. The predetermined time interval, or timeout, for the control algorithm to jump back to the default condition may be anywhere from 1 second to 10 seconds, more often between 2 seconds and 5 seconds.

As can be understood from FIGS. 3 and 4, the handle 100 can consist of two injection molded plastic shell elements, 172a and 172b (see FIG. 2). FIGS. 3 and 4 show one shell element 172a removed to show the interior of the handle 100. It can be seen that annular groove features 174 are provided that engage flanges 175 on rotating assembly 155 to allow for its rotation. The rotating assembly 155 also carries a 3 or 4 axis accelerometer 180 or gyroscope (see FIG. 3) in an interior region thereof, typically proximally spaced apart from the image sensor 125 and lens 127. In order to provide the large number of electrical leads required for the image sensor 125 and the accelerometer 180, two flex circuit ribbons 182A and 182B (dotted lines) are provided and carried within cable sheath 185 that extends away from handle 100. The distal end of the two flex circuit ribbons are connected to rotating assembly 155, therefore, to allow for rotation of the rotating assembly 155 mechanisms are needed to accommodate the needed slack in the flex circuit ribbons 182A and 182B during rotation of the rotating assembly 155 relative to the upper housing 150 (FIGS. 3-4). As can be seen in FIGS. 3-4, the rotating assembly 155 includes a spool 190 around which the flex circuit ribbons 182A and 182B can be coiled or spooled. The spool 190 is formed as a part of the rotating assembly 155. A suitable length of flex circuit ribbons 182A and 182B is provided to allow for at least 90° rotation, or more often 180° or 360° of rotation of the rotating assembly 155 relative to the handle 100. In the variation shown in FIGS. 3-4, it can be seen that a single spool 190 is provided for receiving both flex circuit ribbons 182A and 182B, but it should be appreciated that two separate spools can be formed in the rotating assembly 155 adapted for receiving a slack length of each flex circuit ribbon 182A and 182B.

In a specific example, the image sensor 125 can comprise a sensor from OmniVision, 4275 Burton Drive, Santa Clara, CA 95054 with the part name/number as follows: High- Definition Sensor OV9734 with a 1280×720 pixel count. The sensor 125 has package dimensions of 2532 μm×1722 μm, with a diagonal of approximately 3 mm. In this example, the flex circuit ribbons 182A and 182B are approximately 3.4 mm in width with a 0.2 mm thickness which allows it to spool easily on spool 190.

While the variation of FIGS. 3-4 shows the handle accommodating the flex circuit ribbons 182A and 182B in a spool (or spools), it should be appreciated that the slack portion of the flex circuit ribbons can be configured with at least one of a coiled form, spiral form or folded form without one or more spools.

Referring again to FIGS. 3-4, a second cable 195 extends from the handle component 100 to the base unit 108 which carries electrical leads 198 (dotted line) from the controller 110A to circuit board 200 and thereafter to the actuator panel 115. The cable 195 carries a plurality of leads 198 for carrying signals to and from the actuator buttons and also for LEDs in the actuator panel and buttons.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. An endoscopic system comprising:
   a handle with a rotatable C-mount coupler assembly for coupling to a proximal end of an endoscope;
   an image sensor carried by the rotatable C-mount coupler assembly;
   at least one of an accelerometer and a gyroscope carried by the rotatable C-mount coupler assembly; and
   electrical leads extending from the at least one accelerometer and gyroscope to a fixed location in the handle, wherein the electrical leads are configured with a slack portion in an interior of the handle to accommodate rotation of rotation of the rotatable C-mount coupler assembly therein.

2. The endoscopic system of claim 1 further comprising:
   a controller and an image processor coupled to the image sensor and the at least one accelerometer and gyroscope; and
   a controller algorithm adapted to acquire signals from the at least one accelerometer and gyroscope caused by rotation of the C-mount coupler and thereafter rotate a displayed image in response to the signals to correct an orientation of the displayed image to a selected configuration.

3. The endoscopic system of claim 2 further comprising a fluid management system controlled by the controller, and at least one actuator in the handle for adjusting operating parameters of the fluid management system.

4. The endoscopic system of claim 3 wherein the controller includes algorithms for operating a fluid inflow source and a negative pressure source of the fluid management system to maintain fluid pressure in a working space within a set pressure range.

5. The endoscopic system of claim 1 further comprising electrical leads extending from the image sensor to a fixed location in the handle, wherein the electrical leads are configured with a slack portion in an interior of the handle to accommodate rotation of the rotatable C-mount coupler assembly therein.

6. The endoscopic system of claim 1 wherein the rotatable C-mount coupler assembly is configured to rotate at least 90° about its axis in the handle.

7. The endoscopic system of claim 1 wherein the rotatable C-mount coupler assembly is configured to rotate at least 180° about its axis in the handle.

8. The endoscopic system of claim 1 further comprising a light source adapted for coupling to the endoscope and at least one actuator in the handle for adjusting operating parameters of light source.

9. The endoscopic system of claim 1 further comprising at least one actuator in the handle for operating the image sensor to capture images or videos.

10. An endoscopic system comprising:
    a handle with a rotatable C-mount coupler assembly for coupling to a proximal end of an endoscope;
    an image sensor carried by the rotatable C-mount coupler assembly;
    at least one of an accelerometer and a gyroscope carried by the rotatable C-mount coupler assembly;

a controller and image processor coupled to the image sensor and the at least one accelerometer and gyroscope, wherein a controller algorithm is adapted to acquire signals from the at least one accelerometer and gyroscope caused by rotation of the C-mount coupler and thereafter rotate a displayed image in response to the signals to correct an orientation of the displayed image to a selected configuration; and electrical leads extending from the at least one accelerometer and gyroscope to a fixed location in the handle, wherein the electrical leads are configured with a slack portion in an interior of the handle to accommodate rotation of the rotatable C-mount coupler assembly therein.

11. A method for orienting an endoscope image on a display comprising:

providing a C-mount coupler carrying an image sensor for displaying an image on a display, wherein the C-mount coupler carries at least one of an accelerometer and a gyroscope carried by the C-mount coupler, wherein the C-mount coupler is rotatably disposed in a handle, wherein electrical leads extend from the at least one accelerometer and gyroscope to a fixed location in the handle, wherein the electrical leads are configured with a slack portion in an interior of the handle to accommodate rotation of the rotatable C-mount coupler assembly therein;

attaching the C-mount coupler to an endoscope;

acquiring signals from the at least one accelerometer and gyroscope caused by rotation of the C-mount coupler; and rotating the image on the display in response to the signals to correct an orientation to a selected configuration.

12. The method of claim 11, further comprising rotating the C-mount coupler and manipulating the image electronically.

* * * * *